United States Patent
Yoshida et al.

(10) Patent No.: US 9,531,397 B2
(45) Date of Patent: Dec. 27, 2016

(54) ATOMIC RESONANCE TRANSITION DEVICE, ATOMIC OSCILLATOR, TIMEPIECE, ELECTRONIC APPARATUS AND MOVING OBJECT

(71) Applicant: Seiko Epson Corporation, Tokyo (JP)

(72) Inventors: Hiroyuki Yoshida, Suwa (JP); Nobuhito Hayashi, Chino (JP)

(73) Assignee: Seiko Epson Corporation (JP)

( * ) Notice: Subject to any disclaimer, the term of this patent is extended or adjusted under 35 U.S.C. 154(b) by 0 days.

(21) Appl. No.: 14/973,796

(22) Filed: Dec. 18, 2015

(65) Prior Publication Data

US 2016/0182069 A1 Jun. 23, 2016

(30) Foreign Application Priority Data

Dec. 19, 2014 (JP) ................................ 2014-257006

(51) Int. Cl.
| | |
|---|---|
| *H03B 17/00* | (2006.01) |
| *H03L 7/26* | (2006.01) |
| *G04F 5/14* | (2006.01) |
| *G01N 21/63* | (2006.01) |

(52) U.S. Cl.
CPC ................ *H03L 7/26* (2013.01); *G01N 21/63* (2013.01); *G04F 5/145* (2013.01); *H03B 17/00* (2013.01)

(58) Field of Classification Search
CPC ............. H03B 17/00; H03L 7/26; G04F 5/14; G04F 5/145
USPC ................................................... 331/3, 94.1
See application file for complete search history.

(56) References Cited

U.S. PATENT DOCUMENTS

| | | | | |
|---|---|---|---|---|
| 6,320,472 | B1 | 11/2001 | Vanier | |
| 8,760,232 | B2* | 6/2014 | Chindo | G04F 5/145 |
| | | | | 331/3 |
| 8,831,056 | B2* | 9/2014 | Savchenkov | G04F 5/14 |
| | | | | 372/18 |
| 9,048,853 | B2* | 6/2015 | Chindo | G04F 5/145 |
| 9,197,230 | B2* | 11/2015 | Tanaka | H03L 1/00 |
| 2005/0212607 | A1* | 9/2005 | Happer | G01R 33/26 |
| | | | | 331/94.1 |
| 2009/0289728 | A1* | 11/2009 | Ben-Aroya | H03L 7/26 |
| | | | | 331/94.1 |
| 2011/0187467 | A1 | 8/2011 | Chindo | |

(Continued)

FOREIGN PATENT DOCUMENTS

| | | |
|---|---|---|
| JP | 08-163026 A | 6/1996 |
| JP | 2010-147367 A | 7/2010 |
| JP | 2011-160251 A | 8/2011 |

OTHER PUBLICATIONS

Knappe, S., et al. "Advances in chip-scale atomic frequency references at NIST." Optical Engineering+ Applications. International Society for Optics and Photonics, 2007.*

*Primary Examiner* — Levi Gannon
(74) *Attorney, Agent, or Firm* — Harness, Dickey & Pierce, P.L.C.

(57) ABSTRACT

An atomic resonance transition device includes an atomic cell in which an atom is sealed, a first light source part to emit a first light resonant with a D1 line of the atom in the atomic cell, a second light source part to emit a second light having a wavelength different from that of the first light and resonant with the D1 line or a D2 line of the atom in the atomic cell, and a detection part to detect a light beat due to interference between the first light and the second light passing through the atomic cell and to generate a beat signal.

17 Claims, 10 Drawing Sheets

(56) References Cited

U.S. PATENT DOCUMENTS

| | | | |
|---|---|---|---|
| 2011/0309887 A1* | 12/2011 | Maki | H03L 7/26 |
| | | | 331/94.1 |
| 2012/0229222 A1 | 9/2012 | Balet et al. | |
| 2013/0147565 A1* | 6/2013 | Aoyama | G04F 5/14 |
| | | | 331/94.1 |
| 2015/0091659 A1* | 4/2015 | Kubo | G04F 5/145 |
| | | | 331/94.1 |
| 2015/0180209 A1* | 6/2015 | Takenaka | H01S 5/0425 |
| | | | 372/107 |

* cited by examiner

ATOMIC RESONANCE TRANSITION DEVICE, ATOMIC OSCILLATOR, TIMEPIECE, ELECTRONIC APPARATUS AND MOVING OBJECT

CROSS REFERENCE

This application claim benefit of Japanese Application JP 2014-257006, filed on Dec. 19, 2014. The disclosure of the prior application is hereby incorporated by reference herein in its entirety.

BACKGROUND

1. Technical Field

The present invention relates to an atomic resonance transition device, an atomic oscillator, a timepiece, an electronic apparatus and a moving object.

2. Related Art

As an oscillator with highly accurate oscillation characteristics stable for a long term, an atomic oscillator is known which oscillates based on an energy transition of atoms of alkali metal such as rubidium or cesium.

In general, the operation principle of the atomic oscillator is roughly classified into a system using a double resonance phenomenon caused by light and microwaves and a system using coherent population trapping (CPT) caused by two types of lights having different wavelengths. Since the atomic oscillator using the coherent population trapping can be miniaturized as compared with the atomic oscillator using the double resonance phenomenon, in recent years, the former atomic oscillator is expected to be mounted on various equipments (see, for example, JP-A-2011-160251 (Patent Literature 1)).

As disclosed in, for example, Patent Literature 1, the atomic oscillator using the coherent population trapping includes a gas cell in which a gaseous alkali metal atom is sealed, a light source to emit a resonant light pair (first and second light) for resonating the alkali metal atom in the gas cell, and a light detection part to detect the resonant light pair passing through the gas cell. In the atomic oscillator as stated above, an EIT (Electromagnetically Induced Transparency) phenomenon occurs in which when a frequency difference between two types of resonant lights is a specific value, both the two types of resonant lights are not absorbed by the alkali metal atom in the gas cell and pass through. The light detector detects an EIT signal as a sharp signal generated by the EIT phenomenon, and the EIT signal is used as a reference signal.

Besides, in the atomic oscillator of Patent Literature 1, in order to achieve miniaturization of a circuit portion and power saving, frequency control is performed based on a beat signal obtained by interference between plural lights passing through the gas cell, so that the first and second light become the resonant light pair to cause the EIT phenomenon.

However, in the atomic oscillator using the coherent population trapping, that is, in the atomic oscillator using the EIT signal as the reference signal, a constant magnetic field is generally applied to the alkali metal atom in the gas cell. Thus, also in the atomic oscillator disclosed in Patent Literature 1, a coil for generation the magnetic field, a shield for shielding an external magnetic field and the like are required, and consequently, there is a problem that miniaturization of the device can not be sufficient achieved.

SUMMARY

An advantage of some aspects of the invention is to provide an atomic resonance transition device which can be miniaturized and to provide an atomic oscillator, a timepiece, an electronic apparatus and a moving object, which include the atomic resonance transition device.

The invention can be implemented as following forms or application examples.

Application Example 1

An atomic resonance transition device according to an application example of the invention includes an atomic cell in which an atom is sealed, a first light source part to emit a first light resonant with a D1 line of the atom, a second light source part to emit a second light having a wavelength different from that of the first light and resonant with the D1 line or a D2 line of the atom, and a detection part to detect a light beat due to interference between the first light and the second light passing through the atomic cell and to generate a beat signal.

According to the atomic resonance transition device, an atomic oscillator having highly accurate oscillation characteristics based on atomic energy transition can be realized not by using the EIT signal as the signal due to the electromagnetically induced transparency phenomenon, but by using the beat signal. Thus, components, such as a magnetic coil, a magnetic shield and a polarizing plate, which are required in the related art device using the EIT signal, become unnecessary, and consequently, miniaturization of the device can be achieved. Further, since the light resonant with the D1 line of the atom is used as at least the first light in the first light and the second light, as compared with the case using only the D2 line, a line width of atomic absorption can be narrowed, and consequently, a S/N ratio can be improved.

Application Example 2

In the atomic resonance transition device according to the application example of the invention, it is preferable that the second light is a light resonant with the D2 line of the atom.

With this configuration, a difference between the wavelength of the first light and the wavelength of the second light is increased, and the frequency of the beat signal can be raised. Consequently, short-term stability can be enhanced.

Application Example 3

In the atomic resonance transition device according to the application example of the invention, it is preferable that the second light is a light resonant with the D1 line of the atom.

With this configuration, the line width of atomic absorption can be narrowed for both the first light and the second light.

Application Example 4

In the atomic resonance transition device according to the application example of the invention, it is preferable that the atom is an alkali metal atom.

With this configuration, the line width of atomic absorption can be made relatively narrow. Besides, noise mixed in the beat signal can be reduced.

Application Example 5

In the atomic resonance transition device according to the application example of the invention, it is preferable that the alkali metal atom is a cesium atom.

Among the alkali metals, the cesium atom has a relatively large frequency difference between the D1 line and the D2 line. Thus, the difference between the wavelength of the first light and the wavelength of the second light is increased, and the frequency of the beat signal can be increased.

Application Example 6

It is preferable that the atomic resonance transition device according to the application example of the invention further includes a first control part which controls the first light source part and causes the wavelength of the first light to become a peak wavelength of an absorption spectrum of the atom.

With this configuration, the first light can be resonated with the D1 line of the atom.

Application Example 7

In the atomic resonance transition device according to the application example of the invention, it is preferable that the first control part controls the first light source part and causes the wavelength of the first light to become a peak wavelength of a saturated absorption spectrum of the atom.

With this configuration, the line width of atomic absorption due to the first light can be narrowed.

Application Example 8

It is preferable that the atomic resonance transition device according to the application example of the invention includes a second control part which controls the second light source part and causes the wavelength of the second light to become a peak wavelength of an absorption spectrum of the atom.

With this configuration, the second light can be resonated with the D1 line or the D2 line of the atom.

Application Example 9

In the atomic resonance transition device according to the application example of the invention, it is preferable that the second control part controls the second light source part and causes the wavelength of the second light to become a peak wavelength of a saturated absorption spectrum of the atom.

With this configuration, the line width of atomic absorption due to the second light can be narrowed.

Application Example 10

In the atomic resonance transition device according to the application example of the invention, it is preferable that the first light and the second light intersect each other in the atomic cell.

With this configuration, control can be performed to cause the wavelength of at least one of the first light and the second light to become the saturated absorption spectrum of the atom.

Application Example 11

It is preferable that the atomic resonance transition device according to the application example of the invention further includes an output part to output a clock signal by using the beat signal.

With this configuration, the highly accurate clock signal based on the beat signal can be obtained.

Application Example 12

An atomic oscillator according to an application example of the invention includes the atomic resonance transition device according to the application example of the invention.

With this configuration, the small atomic oscillator can be provided.

Application Example 13

A timepiece according to an application example of the invention includes the atomic resonance transition device according to the application example of the invention.

With this configuration, the small timepiece including the atomic resonance transition device can be provided.

Application Example 14

An electronic apparatus according to an application example of the invention includes the atomic resonance transition device according to the application example of the invention.

With this configuration, the small electronic apparatus including the atomic resonance transition device can be provided.

Application Example 15

A moving object according to an application example of the invention includes the atomic resonance transition device according to the application example of the invention.

With this configuration, the small moving object including the atomic resonance transition device can be provided.

BRIEF DESCRIPTION OF THE DRAWINGS

The invention will be described with reference to the accompanying drawings, wherein like numbers reference like elements.

DESCRIPTION OF EXEMPLARY
EMBODIMENTS

Hereinafter, an atomic resonance transition device, an atomic oscillator, a timepiece, an electronic apparatus and a moving object according to the invention will be described in detail based on embodiments shown in the attached drawings.

1. Atomic Oscillator (Atomic Resonance Transition Device)

First, an atomic oscillator according to the invention (atomic oscillator including an atomic resonance transition device according to the invention) will be described. Incidentally, in the following, although a description is made on an example in which the atomic resonance transition device according to the invention is applied to the atomic oscillator, the atomic resonance transition device according to the invention is not limited to this, and can be applied to, for example, a device such as a magnetic sensor or a quantum memory.

First Embodiment

Figure 1:
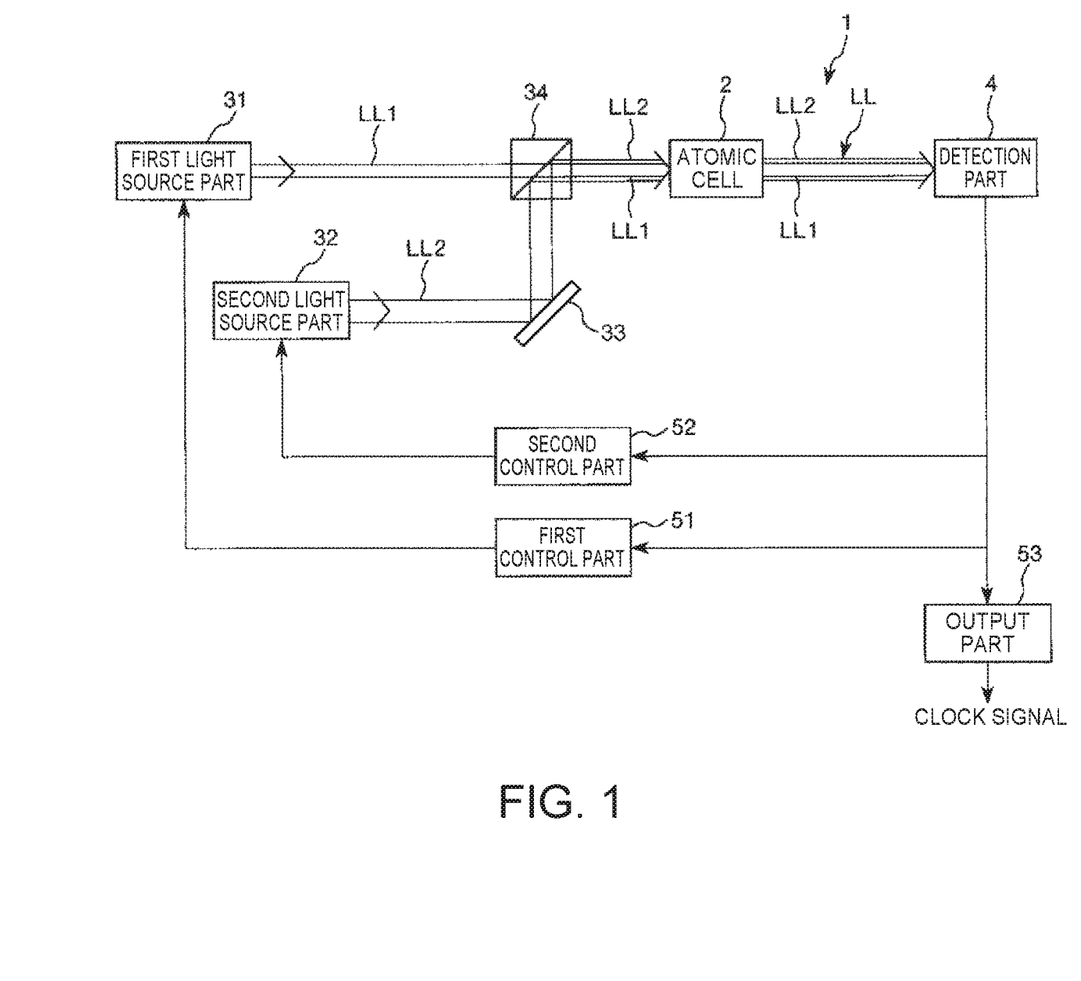
FIG. 1 is a schematic view showing an atomic oscillator (atomic resonance transition device) according to a first embodiment of the invention.
Figure 2:
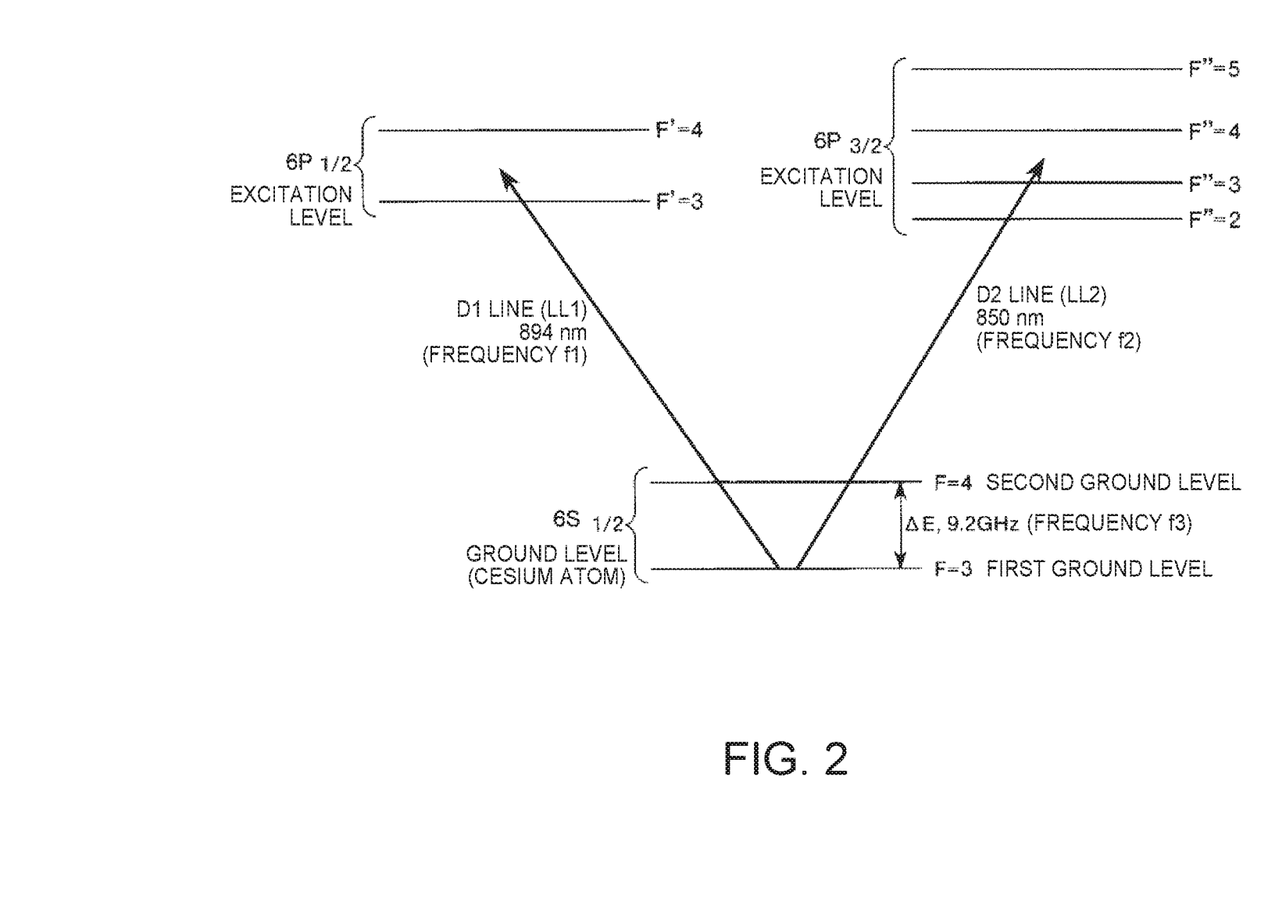
FIG. 2 is a view showing an example of a relation between an energy state of an atom (cesium atom) in an atomic cell and a resonant light pair (first light, second light).
Figure 3:
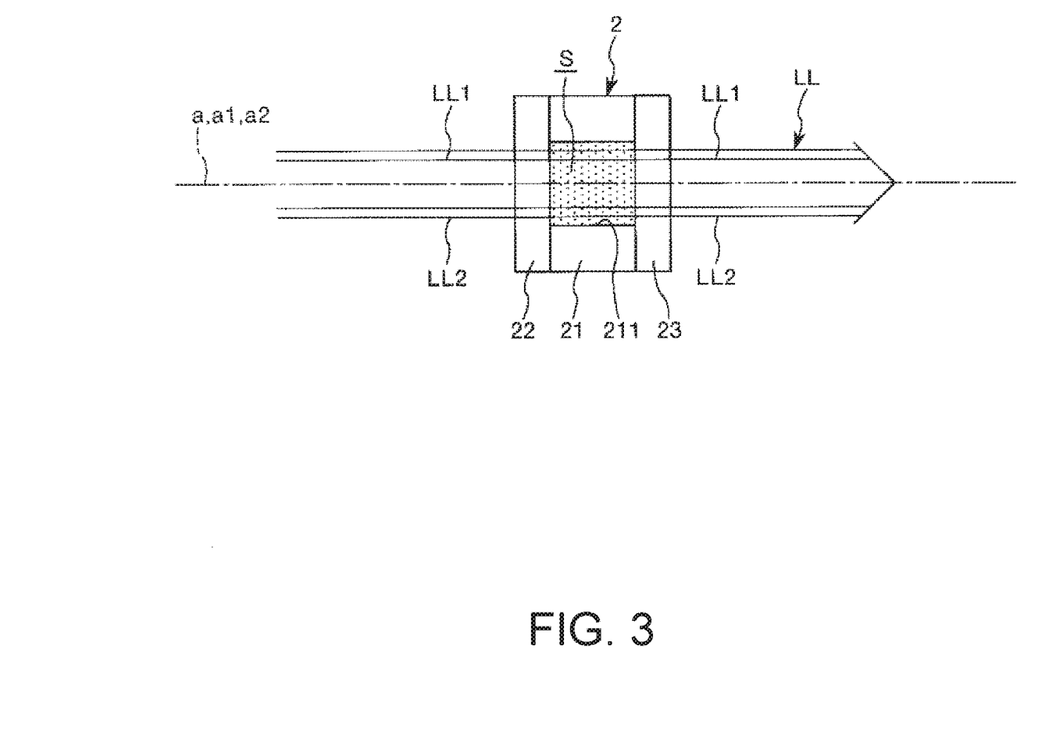
FIG. 3 is a view for explaining lights respectively emitted from a first light source part and a second light source part shown in FIG. 1.
Figure 4:
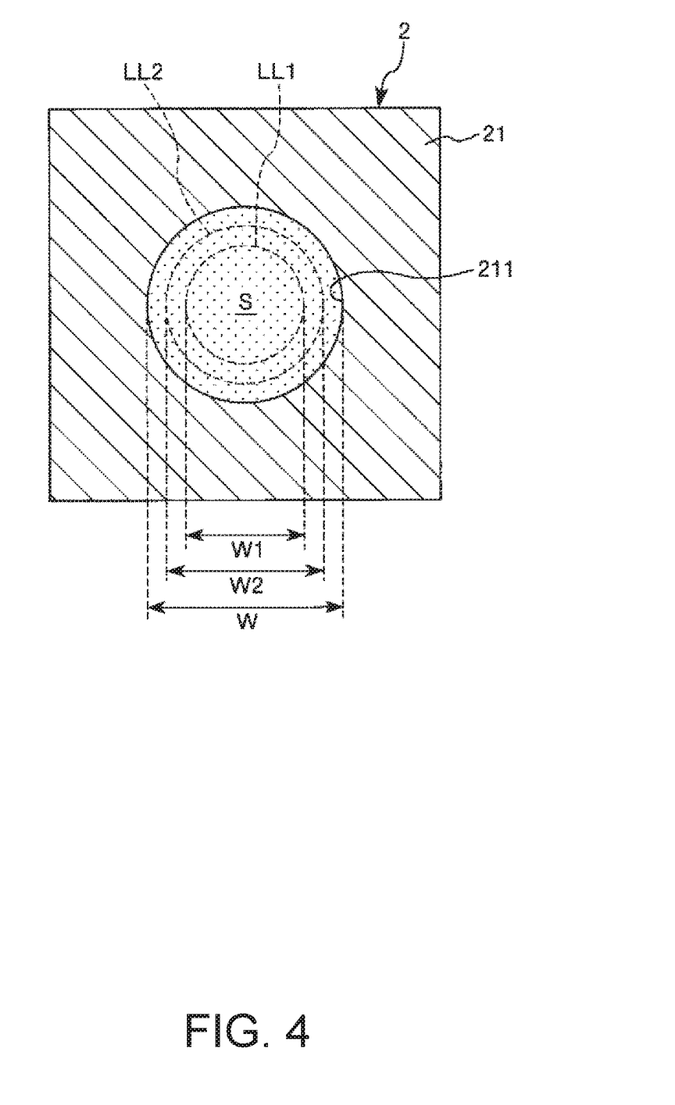
FIG. 4 is a cross-sectional view of an atomic cell shown in FIG. 3.
Figure 5A:
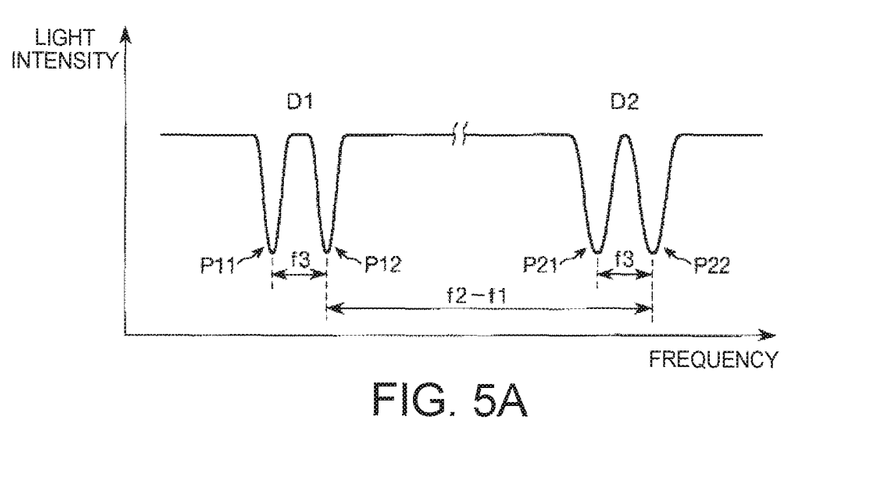
FIG. 5A is a view showing an absorption spectrum of an atom in an atomic cell.
Figure 5B:
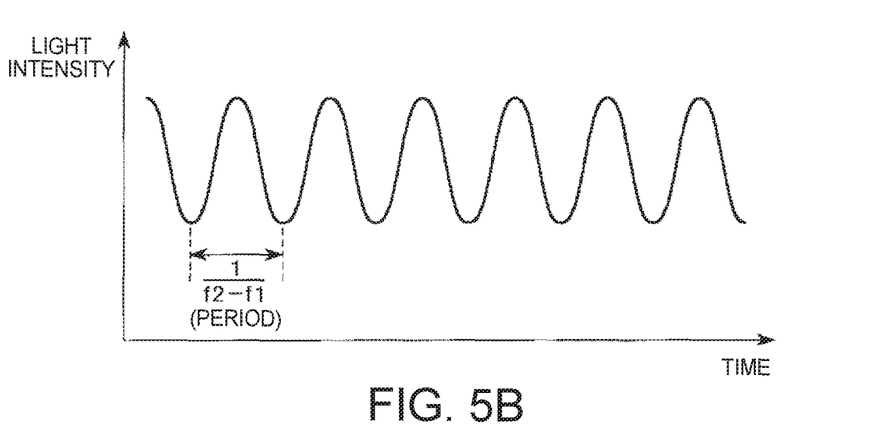
FIG. 5B is a view showing a beat signal detected by a detection part.

FIG. 1 is a schematic view showing an atomic oscillator (atomic resonance transition device) according to a first embodiment of the invention. FIG. 2 is a view showing an example of a relation between an energy state of an atom (cesium atom) in an atomic cell and a resonant light pair (first light, second light). FIG. 3 is a view for explaining lights respectively emitted from a first light source part and a second light source part shown in FIG. 1. FIG. 4 is a cross-sectional view of an atomic cell shown in FIG. 3. FIG. 5A is a view showing an absorption spectrum of an atom in an atomic cell, and FIG. 5B is a view showing a beat signal detected by a detection part.

An atomic oscillator 1 shown in FIG. 1 includes an atomic cell 2 (gas cell) in which an atom is sealed, a first light source part 31 to emit a first light LL1 irradiated to the atom in the atomic cell 2, a second light source part 32 to emit a second light LL2 irradiated to the atom in the atomic cell 2, optical components 33 and 34 to combine the first light LL1 and the second light LL2 and to make the lights incident on the atomic cell 2, a detection part 4 to detect the first light LL1 and the second light LL2 passing through the atomic cell 2, a first control part 51 to control a wavelength of the first light LL1, a second control part 52 to control a wavelength of the second light LL2, and an output part 53 to output a clock signal by using a detection result of the detection part 4.

In the atomic oscillator 1, the wavelength of the first light LL1 emitted from the first light source part 31 and the wavelength of the second light LL2 emitted from the second light source part 32 are different from each other, and the first light LL1 and the second light LL2 overlap each other and generate a beat (light beat LL). Here, the wavelengths of the first light LL1 and the second light LL2 are highly accurately controlled by the first control part 51 and the second control part 52, so that the wavelengths coincide with the absorption spectrum of the atom in the atomic cell 2. Especially, the first light LL1 is controlled to resonate with the D1 line of the atom in the atomic cell 2, and the second light LL2 is controlled to resonate with the D1 line or the D2 line of the atom in the atomic cell 2.

The detection part 4 detects the beat signal equal to the frequency of the light beat LL, and the output part 53 generates and outputs the clock signal by using the beat signal.

According to the atomic oscillator 1, the atomic oscillator having highly accurate oscillation characteristics based on atomic energy transition can be realized not by using the EIT signal as the signal due to the electromagnetically induced transparency phenomenon, but by using the beat signal based on the light beat LL. Accordingly, the EIT signal is not required to be generated. Besides, even if the EIT signal is generated, the EIT signal is not required to be used. Thus, components such as a magnetic coil, a magnetic shield and a polarizing plate, which are required for the related art device using the EIT signal, become unnecessary, and consequently, device miniaturization can be achieved. Further, the light resonant with the D1 line of the atom is used as at least the first light LL1 in the first light LL1 and the second light LL2. Thus, the line width of atomic absorption can be narrowed as compared with the case using only the D2 line, and consequently, the S/N ratio can be improved.

Hereinafter, the respective parts of the atomic oscillator 1 will be described in sequence.

Atomic Cell

Gaseous atoms are sealed in the atomic cell 2. As the atoms, any atom can be used as long as the atom has transition with at least two different resonant wavelengths, that is, the absorption spectrum has at least two peaks. However, from the viewpoint that the line width of the peak of the absorption spectrum is narrow and the gaseous state can be easily formed, an alkali metal such as a rubidium atom, a cesium atom or a sodium atom is preferably used. Besides, a noble gas such as argon or neon and an inert gas such as nitrogen may be sealed as a buffer gas, together with the alkali metal gas, in the atomic cell 2 when necessary. However, from the viewpoint that the line width of the peak of the absorption spectrum is made narrow, atoms other than the alkali metal atom are preferably contained as less as possible in the atomic cell 2. Incidentally, in the following, a description is made on an example where the alkali metal atom is sealed in the atomic cell 2.

For example, a cesium atom as a kind of alkali metal atom has a ground level of $6S_{1/2}$ and two excitation levels of $6P_{1/2}$ and $6P_{3/2}$. Besides, each level of $6S_{1/2}$, $6P_{1/2}$ and $6P_{3/2}$ has a fine structure in which the level is split into plural energy levels. Specifically, the $6S_{1/2}$ level has two ground levels of F=3, 4, the $6P_{1/2}$ level has two excitation levels of F'=3, 4, and the $6P_{3/2}$ level has four excitation levels of F''=2, 3, 4 and 5.

Although the cesium atom in the first ground level of F=3 of $6S_{1/2}$ absorbs the D2 line and can transition to the excitation level of one of F''=2, 3 and 4 of $6P_{3/2}$, the cesium atom can not transition to the excitation level of F''=5. Although the cesium atom in the second ground level of F=4 of $6S_{1/2}$ absorbs the D2 line and can transition to the excitation level of one of F''=3, 4 and 5 of $6P_{3/2}$, the cesium atom can not transition to the excitation level of F''=2. These are according to the transition selection rule assuming electric dipole transition. On the contrary, the cesium atom in the excitation level of one of F''=3, 4 of $6P_{3/2}$ emits the D2 line and can transition to the ground level (original ground level or the other ground level) of F=3 or F=4 of $6S_{1/2}$. The three levels including the two ground levels of F=3, 4 of $6S_{1/2}$ and the excitation level of one of F''=3, 4 of $6P_{3/2}$ are called Λ-type three levels since Λ-type transition by absorption and light emission of the D2 line is possible. Similarly, the three levels including the two ground levels of F=3, 4 of $6S_{1/2}$ and the excitation level of one of F'=3, 4 of $6P_{1/2}$ form the Λ-type three levels since the Λ-type transition by absorption and light emission of the D1 line is possible.

On the other hand, the cesium atom in the excitation level of F'''=2 of $6P_{3/2}$ emits the D2 line and transitions to the ground level (original ground level) of F=3 of $6S_{1/2}$ without fail. Similarly, the cesium atom in the excitation level of F'''=5 of $6P_{3/2}$ emits the D2 line and transitions to the ground level (original ground level) of F=4 of $6S_{1/2}$ without fail. Accordingly, the three levels including the two ground levels of F=3, 4 of $6S_{1/2}$ and the excitation level of F=2 or F=5 of $6P_{3/2}$ do not form the Λ-type three levels since the Λ-type transition by absorption and emission of the D2 line is impossible.

Similarly, an alkali metal atom other than the cesium atom also has two ground levels and one excitation level forming the Λ-type three levels.

As shown in FIG. 3 and FIG. 4, the atomic cell 2 in which the alkali metal is sealed includes a body part 21 and a pair of window parts 22 and 23 provided at both sides of the body part 21. In the atomic cell 2, the body part 21 is disposed between the pair of window parts 22 and 23, and an inner space S in which the gaseous alkali metal is sealed is partitioned (constituted) by the body part 21 and the pair of window parts 22 and 23.

More specifically, the body part 21 has a plate shape, and a through hole 211 passing through the body part 21 in the thickness direction is formed in the body part 21.

A constituent material of the body part 21 is not particularly limited, and glass material, crystal, metal material, resin material, silicon material and the like are mentioned. Particularly, one of the glass material, crystal and silicon material is preferably used, and the silicon material is more preferably used. Hereby, even when the small atomic cell 2 having a width and height of 10 mm or less is formed, the highly accurate body part 21 can be easily formed by using a fine processing technique such as etching. Especially, silicon can be finely processed by etching. Accordingly, when the body part 21 is constituted by using silicon, even if the atomic cell 2 is miniaturized, the body part 21 can be easily and highly accurately formed. Besides, although the window parts 22 and 23 are generally formed of glass, silicon is superior in heat conductivity to the glass. Accordingly, the heat radiation of the body part 21 can be improved. Besides, when the window parts 22 and 23 are formed of glass, the body part 21 and the window parts 22 and 23 can be easily hermetically bonded by anode bonding, and the reliability of the atomic cell 2 can be improved.

The window part 22 is bonded to one surface of the body part 21, and the window part 23 is bonded to the other surface of the body part 21. Hereby, one end opening of the through hole 211 is closed by the window part 22, and the other end opening of the through hole 211 is closed by the window part 23.

The through hole 211 is closed by the window parts 22 and 23 as stated above, so that the inner space S in which the gaseous alkali metal is sealed is formed. In the embodiment, a cross section of the through hole 211, that is, a cross section of the inner space S is circular. Incidentally, the cross sectional shape of the inner space S is not limited to the circle, and may be, for example, a polygon such as a square or a pentagon, an ellipse or the like.

The bonding method of the body part 21 and the window parts 22 and 23 is determined according to the constituent material, and is not particularly limited as long as the hermetic bonding can be performed. For example, a bonding method using an adhesive, a direct bonding method, an anode bonding method, a surface activated bonding method or the like can be used, and the direction bonding method or the anode bonding method is preferably used. Hereby, the body part 21 and the window parts 22 and 23 can be easily hermetically bonded, and the reliability of the atomic cell 2 can be improved.

Each of the window parts 22 and 23 bonded to the body part 21 has a plate shape, and has transparency to the first light LL1 and the second light LL2. The one window part 22 is an incident side window part through which the first light LL1 and the second light LL2 are incident into the inner space S of the atomic cell 2. The other window part 23 is an exit side window part through which the first light LL1 and the second light LL2 exit from the inner space S of the atomic cell 2.

The constituent materials of the window parts 22 and 23 are not particularly limited as long as the materials are transparent to the first light LL1 and the second light LL2. For example, glass material, crystal and the like are mentioned, and the glass material is preferably used. Hereby, the window parts 22 and 23 having excellent transparency to the first light LL1 and the second light LL2 can be realized. Besides, when the body part 21 is formed of silicon, the window parts 22 and 23 are formed by using glass, so that the body part 21 and the window parts 22 and 23 can be easily hermetically bonded by anode bonding, and the reliability of the atomic cell 2 can be improved. Incidentally, the window parts 22 and 23 can also be formed of silicon according to the thicknesses of the window parts 22 and 23 and the intensities of the first light LL1 and the second light LL2. Also in this case, the body part 21 and the window parts 22 and 23 can be directly bonded or anodically bonded.

The atomic cell 2 is controlled to a desired temperature by a not-shown heater. Hereby, the alkali metal in the atomic cell 2 can be kept to be a gaseous state with a desired concentration.

First Light Source Part and Second Light Source Part

The first light source part 31 has a function to emit the first light LL1 (first resonant light) resonant with the D1 line of the atom in the atomic cell 2. On the other hand, the second light source part 32 has a function to emit the second light LL2 (second resonant light) different in wavelength from the first light LL1 and resonant with the D1 line or the D2 line of the atom in the atomic cell 2. Here, each of the first light LL1 and the second light LL2 is light having coherence (coherent properties).

For example, when the atom in the atomic cell 2 is a cesium atom, the wavelength of the first light LL1 is 894 nm resonant with the D1 line (transition from the first ground level to the $6P_{1/2}$ excitation level), and the wavelength of the second light LL2 is 850 nm resonant with the D2 line (transition from the first ground level to the $6P_{3/2}$ excitation level) (see FIG. 2). Incidentally, the wavelength of the second light LL2 may be a wavelength resonant with the D1 line (transition from the second ground level to the $6P_{1/2}$ excitation level), and this wavelength is different from the wavelength of the first light LL1 by a wavelength corresponding to an energy difference ΔE between the first ground level and the second ground level.

The first light source part 31 and the second light source part 32 are not particularly limited as long as the foregoing lights can be emitted, and can be constructed by using, for example, a semiconductor laser such as an end face emitting laser or a vertical cavity surface emitting laser (VCSEL).

Optical Components

The optical component 33 is, for example, a mirror, and the optical component 34 is, for example, a polarizing beam splitter.

The optical component 33 reflects the second light LL2 from the second light source part 32 toward the optical component 34. The optical component 34 allows the first light LL1 from the first light source part 31 to pass through and makes the light incident on the atomic cell 2, and further causes the second light LL2 reflected by the optical component 33 to be reflected and to be incident on the atomic cell 2. Accordingly, as shown in FIG. 3, the first light LL1 and the second light LL2 are combined so that the optical axes are coincident (or parallel) with each other, and the lights are incident on the atomic cell 2.

Here, the optical components 33 and 34 constitute a combining part to combine the first light LL1 and the second light LL2. The combining part causes the optical axes of the first light LL1 and the second light LL2 to be coincident with each other and can irradiate the lights to the atomic cell 2. Incidentally, the optical component 33 may be omitted. In this case, the second optical source part 32 has only to be installed in such a direction that the second light LL2 is incident on the optical component 34.

With respect to the first light LL1 and the second light LL2 combined in this way, the optical axes are coincident or parallel with each other, and the wavelengths are different from each other. Thus, the lights become the light beat LL (beat signal light) by interference. Although FIG. 3 shows a case where an optical axis a1 of the first light LL1 and an optical axis a2 of the second light LL2 are coincident with a center axis "a" of the atomic cell 2, these axes have only to be parallel with each other.

In FIG. 3 and FIG. 4, with respect to the first light LL1 and the second light LL2 combined, although a passing area of the first light LL1 is contained in a passing area of the second light LL2, these passing areas may be coincident with each other, or the passing area of the second light LL2 may be contained in the passing area of the first light LL1, or part of the light passing areas may overlap with each other. Here, from the viewpoint of efficiently causing interference, a width W1 of the first light LL1 is preferably as close to a width W2 of the second light LL2 as possible in the atomic cell 2, and specifically, the width W1 is preferably 0.8 or more and 1.2 or less of the width W2. Besides, each of the width W1 and the width W2 is preferably smaller than a width W in the atomic cell 2, and specifically, each width is preferably 0.5 or more and 0.99 or less of the width W.

Detection Part

The detection part 4 has a function to detect the intensity of the first light LL1 and the second light LL2 passing through the atomic cell 2.

Here, the first light LL1 and the second light LL2 passing through the atomic cell 2 become the light beat LL (beat signal light) by interference as described before. The detection part 4 has a function to detect the light beat LL and to generate and output a detection signal including a beat signal of a frequency equal to a frequency of beat (beat frequency) of the light beat LL.

For example, when the atom in the atomic cell 2 is an alkali metal atom, as shown in FIG. 5A, the absorption spectrum has two adjacent peaks P11 and P12 due to the D1 line and two adjacent peaks P21 and P22 due to the D2 line. The peak P11 corresponds to the transition from the second ground level to the $6P_{1/2}$ excitation level shown in FIG. 2, the peak P12 corresponds to the transition from the first ground level to the $6P_{1/2}$ excitation level shown in FIG. 2, the peak P21 corresponds to the transition from the second ground level to the $6P_{3/2}$ excitation level shown in FIG. 2, and the peak P22 corresponds to the transition from the first ground level to the $6P_{3/2}$ excitation level shown in FIG. 2.

Accordingly, for example, as shown in FIG. 2, when the D1 line transitioning from the first ground level to the $6P_{1/2}$ excitation level is used as the first light LL1, and the D2 line transitioning from the first ground level to the $6P_{3/2}$ excitation level is used as the second light LL2, a difference between the frequency of the peak P12 and the frequency of the peak P22 becomes a difference (f2−f1) between a frequency f1 of the first light LL1 and a frequency f2 of the second light LL2. For example, when the atom in the atomic cell 2 is a cesium atom, the frequency difference (f2−f1) is 16.6 THz. When the atom in the atomic cell 2 is a sodium atom, the frequency difference (f2−f1) is 515 GHz. When the atom in the atomic cell 2 is a rubidium atom, the frequency difference (f2−f1) is 7.12 THz.

As shown in FIG. 5B, the beat frequency of the light beam LL becomes the frequency equal to the frequency difference (f2−f1). That is, the period of the light beat LL becomes 1/(f2−f1).

Incidentally, when the D1 line transitioning from the first ground level to the $6P_{1/2}$ excitation level is used as the first light LL1, and the D1 line transitioning from the second ground level to the $6P_{1/2}$ excitation level is used as the second light LL2, the beat frequency of the light beat LL becomes a frequency equal to a frequency f3 corresponding a difference between the frequency of the peak P11 and the frequency of the peak P12, that is, an energy difference ΔE between the first ground level and the second ground level shown in FIG. 2. For example, when the atom in the atomic cell 2 is a cesium atom, the frequency f3 is 9.2 GHz. When the atom in the atomic cell 2 is a sodium atom, the frequency f3 is 1.7716 GHz. When the atom in the atomic cell 2 is a rubidium ($^{85}$Rb) atom, the frequency f3 is 3.0357 GHz. When the atom in the atomic cell 2 is a rubidium ($^{87}$Rb) atom, the frequency f3 is 6.8346 GHz.

Besides, the line width of each of the peaks P11 and P12 is narrower than the line width of each of the peaks P21 and P22.

Although the detection part 4 is not particularly limited as long as the absorption spectrum and the light beat LL can be detected, for example, a photodetector (high-speed light receiving element) such as a photodiode can be used.

First Control Part and Second Control Part

The first control part 51 has a function to control the first light source part 31 by using the detection result of the detection part 4. Similarly, the second control part 52 has a function to control the second light source part 32 by using the detection result of the detection part 4.

More specifically, the first control part 51 uses the detection result of the detection part 4 and controls the first light source part 31 so that the wavelength of the first light LL1 becomes the peak wavelength (for example, the wavelength of the peak P12 shown in FIG. 5A) of the absorption spectrum of the atom in the atomic cell 2. Hereby, the first light LL1 can be resonated with the D1 line of the atom in the atomic cell 2.

Besides, the second control part 52 uses the detection result of the detection part 4 and controls the second light source part 32 so that the wavelength of the second light LL2 becomes the peak wavelength (for example, the wavelength of the peak P22 shown in FIG. 5A) of the absorption spectrum of the atom in the atomic cell 2. Hereby, the second light LL2 can be resonated with the D2 line of the atom in the atomic cell 2.

Each of the first control part 51 and the second control part 52 can be constructed to include a detection circuit, a modulation circuit and a low-frequency oscillator. The control circuits set bias currents of semiconductor lasers included in the first light source 31 and the second light source 32 by a feedback loop, and adjust the center wavelengths of the first light LL1 and the second light LL2 to the foregoing wavelengths.

Incidentally, in the embodiment, although the first control part 51 and the second control part 52 control the first light source part 31 and the second light source part 32 by using the detection result of the detection part 4, the control parts may control the first light source part 31 and the second light source part 32 by using a detection result of a detection part (light-receiving element) provided separately from the detection part 4. In this case, for example, a polarizing beam splitter is disposed between the atomic cell 2 and the detection part 4, and the branched light beat LL has only to be received by the separately provided detection part.

Output Part

The output part 53 has a function to output a clock signal by using the detection result of the detection part 4. Hereby, the highly accurate clock signal based on the beat signal can be obtained.

Specifically, the output part 53 divides the beat signal included in the detection signal of the detection part 4, and generates and outputs the clock signal (for example, clock signal of 10 MHz or 1 Hz).

The output part 53 can be constructed to include, for example, a flip-flop circuit and a DDS (Direct Digital Synthesizer). Besides, when necessary, the output part 53 may include another circuit such as a filter to select and extract only the beat signal from the detection signal of the detection part 4 or a signal amplifying circuit to amplify the beat signal.

According to the atomic oscillator 1 as described above, the atomic oscillator having highly accurate oscillation characteristics based on the atomic energy transition can be realized not by using the EIT signal as the signal due to the electromagnetically induced transparency phenomenon, but by using the beat signal. Accordingly, the EIT signal is not required to be generated. Besides, even if the EIT signal is generated, the EIT signal is not required to be used. Thus, components such as a magnetic coil, a magnetic shield and a polarizing plate, which are required for the related art device using the EIT signal, become unnecessary, and consequently, device miniaturization can be achieved. Further, the light resonant with the D1 line of the atom is used as at least the first light LL1 in the first light LL1 and the second light LL2. Thus, the line width of atomic absorption can be narrowed as compared with the case using only the D2 line, and consequently, the S/N ratio can be improved.

Here, when the second light LL2 is the light resonant with the D2 line of the atom, the difference between the wavelength of the first light LL1 and the wavelength of the second light LL2 is increased, and the frequency of the beat signal can be raised (increased). Consequently, short-term stability can be enhanced.

On the other hand, when the second light LL2 is the light resonant with the D1 line of the atom, the line width of atomic absorption can be narrowed for both the first light LL1 and the second light LL2.

Besides, when the atom in the atomic cell 2 is the alkali metal atom, the line width of atomic absorption can be relatively easily narrowed. Besides, noise mixed in the beat signal can be reduced. Especially, among the alkali metals, the cesium atom has a relatively large frequency difference between the D1 line and the D2 line. Thus, when the first light LL1 is the D1 line, and the second light LL2 is the D2 line, since the atom in the atomic cell 2 is the cesium atom, the difference between the wavelength of the first light LL1 and the wavelength of the second light LL2 is increased, and the frequency of the beat signal can be raised.

Second Embodiment

Next, a second embodiment will be described.

Figure 6:
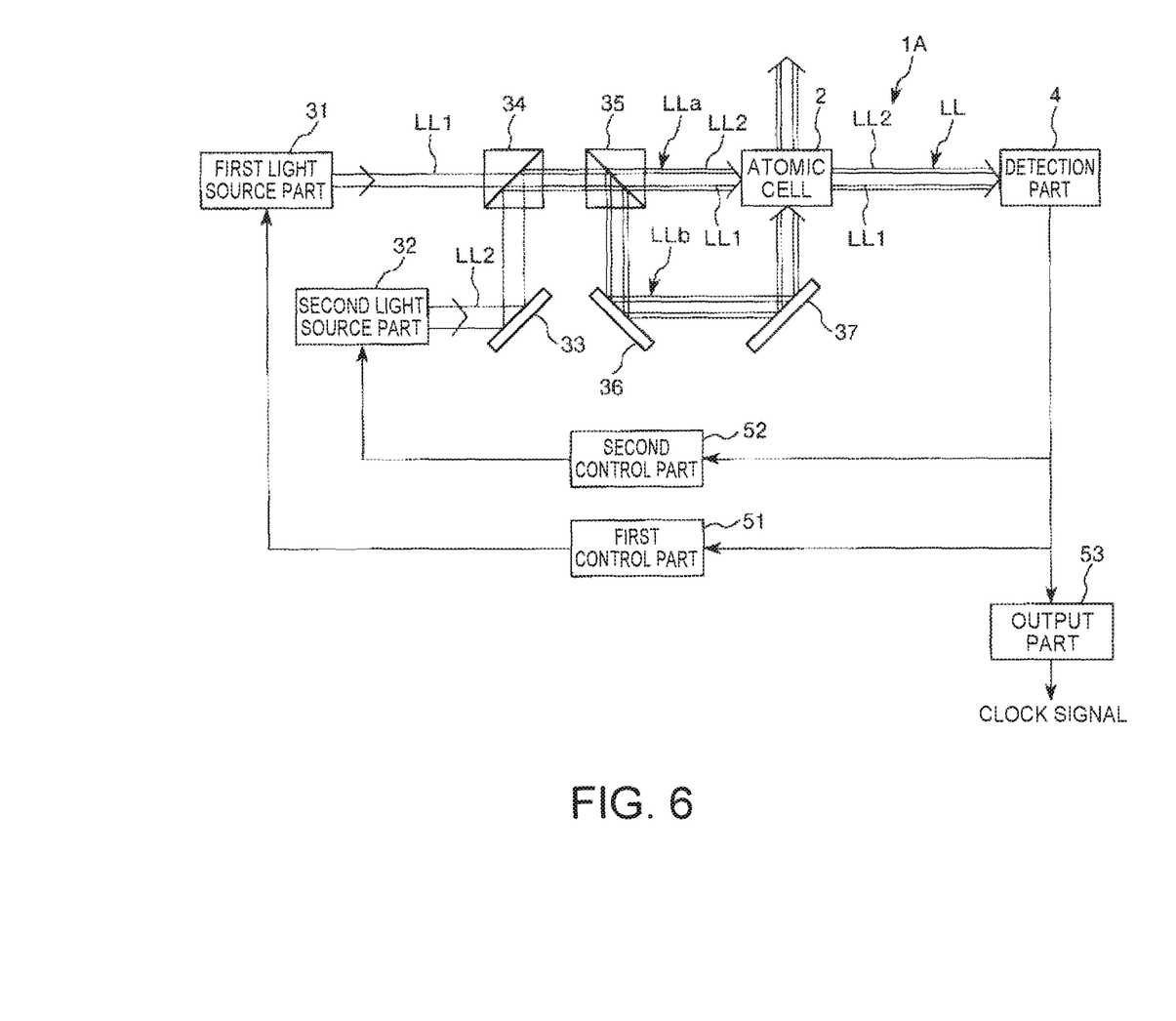
FIG. 6 is a schematic view showing an atomic oscillator (atomic resonance transition device) according to a second embodiment of the invention.
Figure 7:
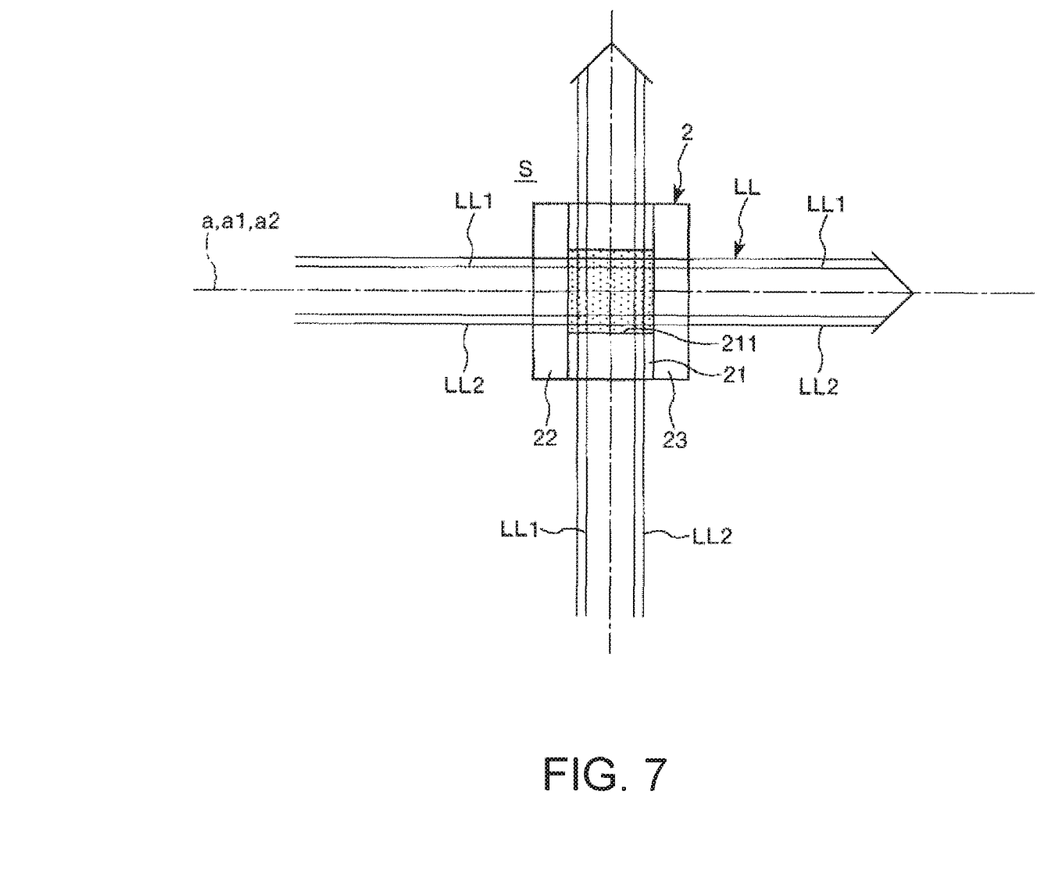
FIG. 7 is a view for explaining lights respectively emitted from a first light source part and a second light source part shown in FIG. 6.

FIG. 6 is a schematic view showing an atomic oscillator (atomic resonance transition device) of the second embodiment of the invention, and FIG. 7 is a view for explaining lights respectively emitted from a first light source part and a second light source part shown in FIG. 6.

This embodiment is the same as the first embodiment except that wavelengths of a first light and a second light are controlled by using a saturated absorption spectrum.

Incidentally, in the following description, with respect to the second embodiment, different points from the foregoing embodiment will be mainly described, and the description of the same matters is omitted. Besides, in FIGS. 6 and 7, the same components as those of the foregoing embodiment are denoted by the same reference numerals.

An atomic oscillator 1A shown in FIG. 6 includes optical components 35, 36 and 37 which are arranged between an optical component 34 and an atomic cell 2 and branch a first light LL1 and a second light LL2 so that the atomic cell 2 is irradiated from two different directions.

The optical component 35 is, for example, a polarizing beam splitter, and the optical components 36 and 37 are respectively, for example, mirrors.

The optical component 35 allows the first light LL1 and the second light LL2 from the optical component 34 to pass through and cause the lights to be incident on the atomic cell 2, and further reflects the lights toward the optical component 36. That is, the optical component 35 branches the light including the first light LL1 and the second light LL2 from the optical component 34 into a light LLa incident on the atomic cell 2 and a light LLb incident on the optical component 36. The light LLa is received by a detection part 4 through the atomic cell 2. On the other hand, the light LLb is reflected by the optical component 37 and is incident on the atomic cell 2 in a direction different from the light LLa as shown in FIG. 7. The light LLb passing through the atomic cell 2 is incident on a not-shown reflection preventing part. FIG. 7 shows a case where the optical axis of the light LLa and the optical axis of the light LLb intersect each other perpendicularly in the atomic cell 2. Incidentally, the optical axis of the light LLb has only to be different in direction from the optical axis of the light LLa, and no limitation is made to the illustration. Besides, in the embodiment, a body part 21 of the atomic cell 2 is constructed to have transparency to the light LLb.

The light LLb is made incident on the atomic cell 2 from the direction different from the light LLa, so that the detection part 4 can detect the peak of the saturated absorption spectrum of the atom in the atomic cell 2. The line width of the peak of the saturated absorption spectrum is narrower than that of the peak of the normal absorption spectrum.

A first control part 51 controls a first light source part 31 so that the wavelength of the first light LL1 becomes the peak wavelength of the saturated absorption spectrum of the atom in the atomic cell 2. Hereby, the line width of atomic absorption due to the first light LL1 can be narrowed. Similarly, a second control part 52 controls a second light source part 32 so that the wavelength of the second light LL2 becomes the peak wavelength of the saturated absorption spectrum of the atom in the atomic cell 2. Hereby, the line width of atomic absorption due to the second light LL2 can be narrowed. Consequently, short-term frequency stability can be improved.

As described above, since the first light LL1 and the second light LL2 intersect each other in the atomic cell 2, control can be performed so that the wavelengths of the first light LL1 and the second light LL2 become the peak wavelengths of the saturated absorption spectrum of the atom in the atomic cell 2.

Also according to the second embodiment as described above, miniaturization can be realized.

2. Timepiece

Figure 8:
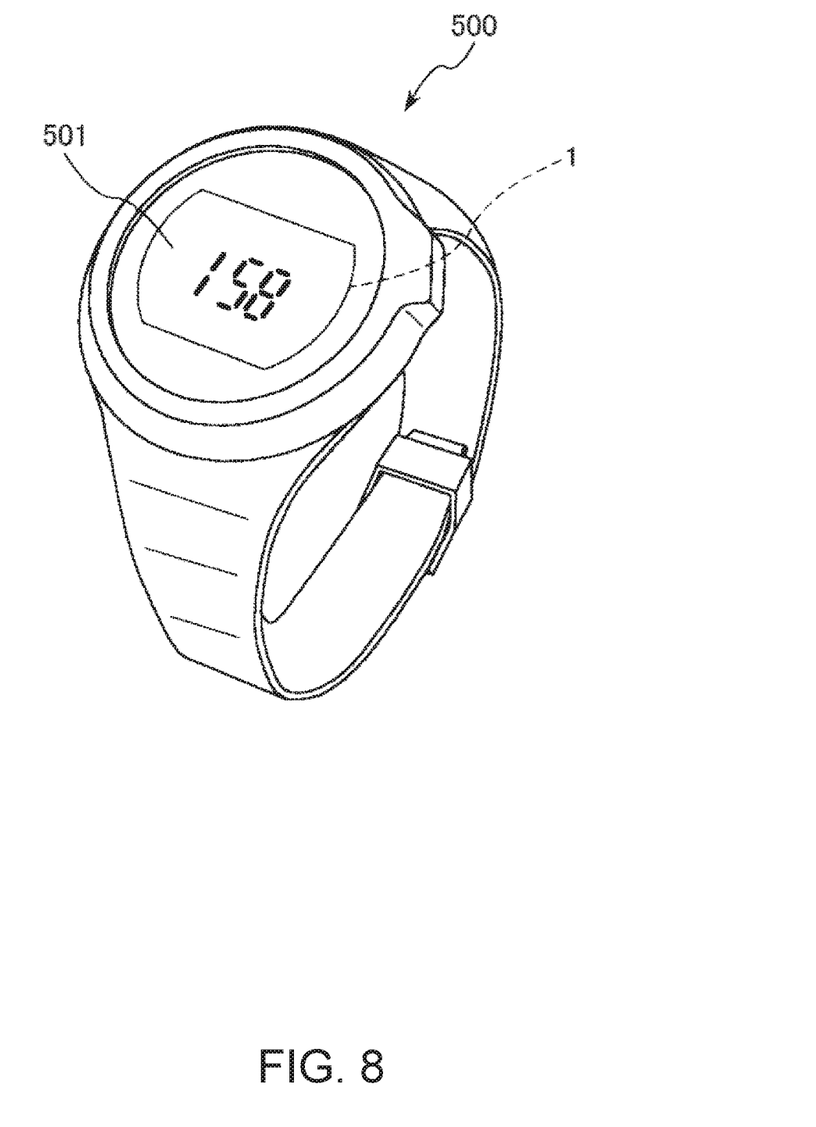
FIG. 8 is a perspective view showing an example of a timepiece according to the invention.

Next, an example of a timepiece according to the invention will be described. FIG. 8 is a perspective view showing an example of the timepiece according to the invention.

A timepiece 500 is a wrist watch and can be mounted on a wrist. The timepiece 500 is equipped with an atomic oscillator 1 miniaturized as described above, and the time based on a clock signal outputted from the atomic oscillator 1 can be displayed on a display part 501.

3. Electronic Apparatus

Figure 9:
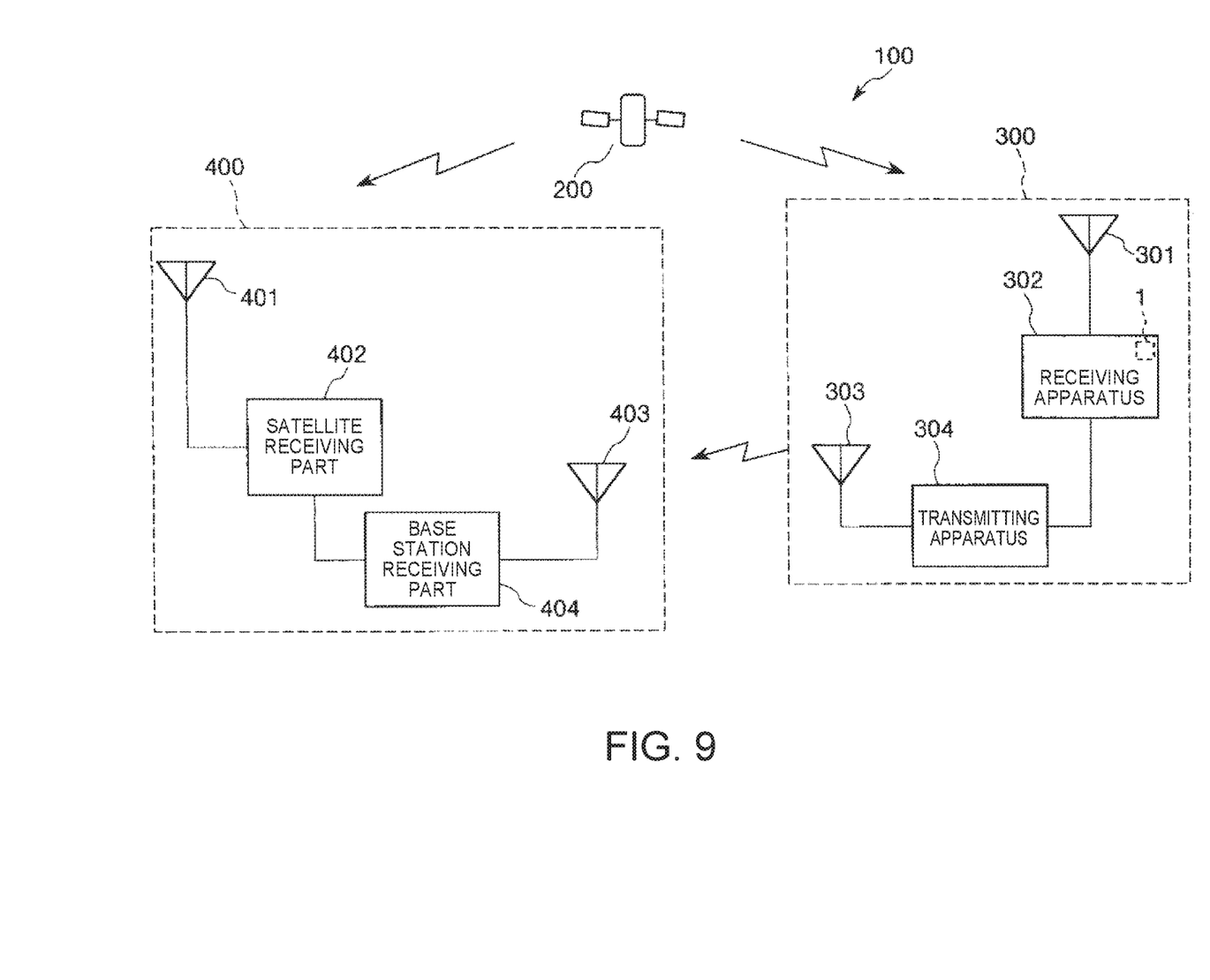
FIG. 9 is a view showing a schematic structure in a case where the atomic oscillator according to the invention is used for a positioning system using a GPS satellite.

FIG. 9 is a view showing a schematic structure in a case where the atomic oscillator according to the invention is used for a positioning system using a GPS satellite.

A positioning system 100 shown in FIG. 9 includes a GPS satellite 200, a base station apparatus 300 and a GPS receiving apparatus 400.

The GPS satellite 200 transmits positioning information (GPS signal).

The base station apparatus 300 includes a receiving apparatus 302 to receive positioning information with high accuracy from the GPS satellite 200 through an antenna 301 installed at, for example, an electronic reference point (GPS continuous observation station), and a transmitting apparatus 304 to transmit the positioning information received by the receiving apparatus 202 through an antenna 303.

Here, the receiving apparatus 202 is an electronic apparatus including the atomic oscillator 1 according to the invention as the reference frequency oscillation source. The receiving apparatus 302 has excellent reliability. Besides, the positioning information received by the receiving apparatus 302 is transmitted by the transmitting apparatus 304 in real time.

The GPS receiving apparatus 400 includes a satellite receiving part 402 to receive the positioning information from the GPS satellite 200 through an antenna 401, and a base station receiving part 404 to receive the positioning information from the base station apparatus 300 through an antenna 403.

4. Moving Object

Figure 10:
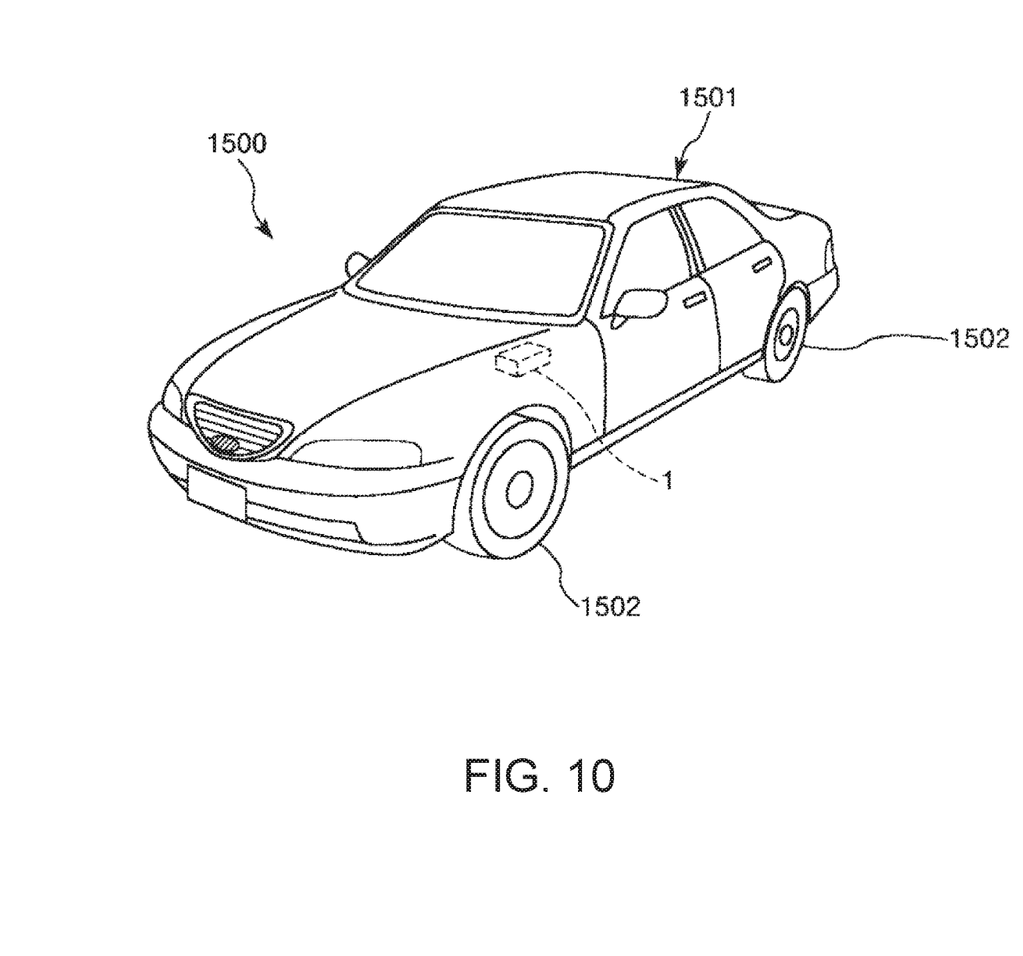
FIG. 10 is a view showing an example of a moving object according to the invention.

FIG. 10 is a view showing an example of a moving object according to the invention.

In the drawing, a moving object 1500 includes a vehicle body 1501 and four wheels 1502, and the wheels 1502 are rotated by a not-shown power source (engine) provided in the vehicle body 1501. The moving object 1500 has a built-in atomic oscillator 1.

Incidentally, the electronic apparatus according to the invention is not limited to the foregoing, and can be applied to, for example, a cellular phone, digital still camera, ink-jet discharge apparatus (for example, ink-jet printer), personal computer (mobile personal computer, lap-top personal computer), television, video camera, video tape recorder, car navigation apparatus, pager, electronic notebook (also including one with communication function), electronic dictionary, electronic calculator, electronic game equipment, word processor, work station, video telephone, crime prevention video monitor, electronic binoculars, POS terminal, medical equipment (for example, electronic thermometer, blood pressure meter, blood sugar meter, electrocardiographic apparatus, ultrasound diagnosis apparatus, electronic endoscope), fish finder, various measuring equipments, instruments (for example, instruments for vehicle, airplane or ship), flight simulator, terrestrial digital broadcast, cellular phone base station, GPS module and the like.

In the above, although the atomic resonance transition device, the atomic oscillator, the timepiece, the electronic apparatus and the moving object according to the invention are described based on the illustrated embodiments, the invention is not limited to these.

Besides, the respective components of the invention can be replaced by arbitrary ones having the same function as those of the foregoing embodiments, and arbitrary components can be added. Besides, in the invention, arbitrary components of the foregoing respective embodiments may be combined.

What is claimed is:

1. An atomic resonance transition device, comprising:
    an atomic cell in which an atom is sealed;
    a first light source that is configured to emit a first light resonant with a D1 line of the atom;
    a second light source that is configured to emit a second light having a wavelength different from that of the first light and resonant with the D1 line or a D2 line of the atom;
    a detector that is configured to detect a light beat due to interference between the first light and the second light passing through the atomic cell and to generate a beat signal;
    a first controller that is configured to control the first light source and causes the wavelength of the first light to become a peak wavelength of an absorption spectrum of the atom; and
    a second controller that is configured to control the second light source and causes the wavelength of the second light to become the peak wavelength of the absorption spectrum of the atom.

2. The atomic resonance transition device according to claim 1, wherein the second light is a light resonant with the D2 line of the atom.

3. An atomic oscillator comprising an atomic resonance transition device according to claim 2.

4. A timepiece comprising an atomic resonance transition device according to claim 2.

5. An electronic apparatus comprising an atomic resonance transition device according to claim 2.

6. A moving object comprising an atomic resonance transition device according to claim 2.

7. The atomic resonance transition device according to claim 1, wherein the second light is a light resonant with the D1 line of the atom.

8. The atomic resonance transition device according to claim 1, wherein the atom is an alkali metal atom.

9. The atomic resonance transition device according to claim 8, wherein the alkali metal atom is a cesium atom.

10. The atomic resonance transition device according to claim 1, wherein the first controller is configured to control the first light source and causes the wavelength of the first light to become a peak wavelength of a saturated absorption spectrum of the atom.

11. The atomic resonance transition device according to claim 10, wherein the first light and the second light intersect each other in the atomic cell.

12. The atomic resonance transition device according to claim 1, wherein the second controller is configured to control the second light source and causes the wavelength of the second light to become a peak wavelength of a saturated absorption spectrum of the atom.

13. The atomic resonance transition device according to claim 1, further comprising an output part to output a clock signal by using the beat signal.

14. An atomic oscillator comprising an atomic resonance transition device according to claim 1.

15. A timepiece comprising an atomic resonance transition device according to claim 1.

16. An electronic apparatus comprising an atomic resonance transition device according to claim 1.

17. A moving object comprising an atomic resonance transition device according to claim 1.

* * * * *